United States Patent
Etoh et al.

(10) Patent No.: US 10,215,733 B2
(45) Date of Patent: Feb. 26, 2019

(54) NON-DESTRUCTIVE TESTING METHOD AND A NON-DESTRUCTIVE TESTING DEVICE FOR AN ANCHOR BOLT

(71) Applicant: NUCLEAR FUEL INDUSTRIES, LIMITED, Tokyo (JP)

(72) Inventors: Junji Etoh, Sennan-gun (JP); Takashi Matsunaga, Sennan-gun (JP); Ryota Ogawa, Sennan-gun (JP); Yoshihiro Isobe, Sennan-gun (JP); Mitsuyuki Sagisaka, Sennan-gun (JP)

(73) Assignee: NUCLEAR FUEL INDUSTRIES, LIMITED, Tokyo (JP)

( * ) Notice: Subject to any disclaimer, the term of this patent is extended or adjusted under 35 U.S.C. 154(b) by 83 days.

(21) Appl. No.: 15/327,238

(22) PCT Filed: Feb. 3, 2015

(86) PCT No.: PCT/JP2015/052913
§ 371 (c)(1),
(2) Date: Jan. 18, 2017

(87) PCT Pub. No.: WO2016/013236
PCT Pub. Date: Jan. 28, 2016

(65) Prior Publication Data
US 2017/0160238 A1 Jun. 8, 2017

(30) Foreign Application Priority Data
Jul. 22, 2014 (JP) ................................. 2014-148607

(51) Int. Cl.
*G01N 29/46* (2006.01)
*G01N 29/44* (2006.01)
*G01N 29/11* (2006.01)
*G01N 29/12* (2006.01)
*G01N 29/04* (2006.01)

(52) U.S. Cl.
CPC .......... *G01N 29/045* (2013.01); *G01N 29/11* (2013.01); *G01N 29/12* (2013.01);
(Continued)

(58) Field of Classification Search
CPC ................. G01N 29/045; G01N 29/12; G01N 2291/2691
(Continued)

(56) References Cited

U.S. PATENT DOCUMENTS 4,062,229 A    12/1977   Godfrey et al.
4,198,865 A *  4/1980    Tarpley, Jr. ............. G01N 3/32
                                                              73/582
(Continued)

FOREIGN PATENT DOCUMENTS

JP        10090234       *  4/1998
JP        2000-88817 A      3/2000
(Continued)

OTHER PUBLICATIONS

Japanese Notification of Reasons for Refusal, dated Jul. 10, 2017, for Japanese Application No. 2014-148607, as well as a English machine translation.
(Continued)

*Primary Examiner* — J M Saint Surin
(74) *Attorney, Agent, or Firm* — Birch, Stewart, Kolasch & Birch LLP

(57) ABSTRACT

The purpose of the present invention is to provide a nondestructive inspection method and nondestructive inspection device for an anchor bolt capable of quantitatively inspecting the health of an anchor bolt fixed to a foundation by a metallic anchor. Provided is a nondestructive anchor-bolt inspection method for inspecting the health of an anchor bolt fixed to a foundation by a metallic anchor, wherein a striking sound is produced through the striking of a portion of the
(Continued)

anchor bolt exposed from the surface of the foundation, frequency information is obtained through the reception and frequency analysis of the signal waveform of the striking sound, and the health of the anchor bolt is nondestructively and quantitatively inspected on the basis of the frequency information for the signal waveform. Also provided is a nondestructive inspection device for an anchor bolt.

6 Claims, 3 Drawing Sheets

(52) U.S. Cl.
CPC ......... *G01N 29/4427* (2013.01); *G01N 29/46* (2013.01); *G01N 2291/015* (2013.01); *G01N 2291/0234* (2013.01); *G01N 2291/0258* (2013.01); *G01N 2291/044* (2013.01); *G01N 2291/101* (2013.01); *G01N 2291/2691* (2013.01)

(58) Field of Classification Search
USPC .......................................................... 73/593
See application file for complete search history.

(56) References Cited

U.S. PATENT DOCUMENTS

| | | | | |
|---|---|---|---|---|
| 5,798,881 A | * | 8/1998 | Mazurek | B60R 1/087 248/474 |
| 7,152,475 B2 | * | 12/2006 | Nakamura | G01L 5/246 73/581 |
| 8,671,761 B2 | * | 3/2014 | Zagrai | G01N 29/2437 73/597 |
| 8,807,877 B1 | * | 8/2014 | Fox | E21D 21/0026 405/259.1 |

FOREIGN PATENT DOCUMENTS

| | | | |
|---|---|---|---|
| JP | 2000-131293 A | | 5/2000 |
| JP | 2004037287 | * | 2/2004 |
| JP | 2004-77234 A | | 3/2004 |
| JP | 2004-325224 A | | 11/2004 |
| JP | 2010-203810 A | | 9/2010 |
| JP | 20100203810 | * | 9/2010 |
| JP | 2014202682 | * | 10/2014 |
| JP | 2015064351 | * | 4/2015 |
| JP | 5897199 | * | 3/2016 |

OTHER PUBLICATIONS

Etoh et al., "Development of a new inspection system for adhesive anchor bolts based on hammering tests (1) Experimental studies", Atomic Energy Society of Japan Haru no Nenkai Yokoshu (CD-ROM), Mar. 10, 2014 (received date), vol. 2014, p. ROMBUNNO. L43.
International Search Report, issued in PCT/JP2015/052913 (PCT/ISA/210), dated Apr. 21, 2015.
Written Opinion of the International Searching Authority, issued in PCT/JP2015/052913 (PCT/ISA/237), dated Apr. 21, 2015.

* cited by examiner

[FIG.1]
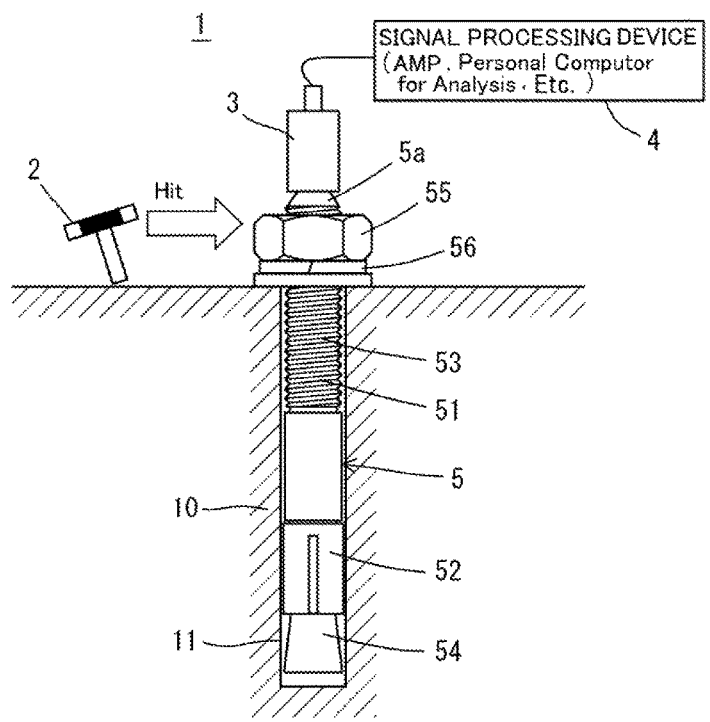
[FIG.2]
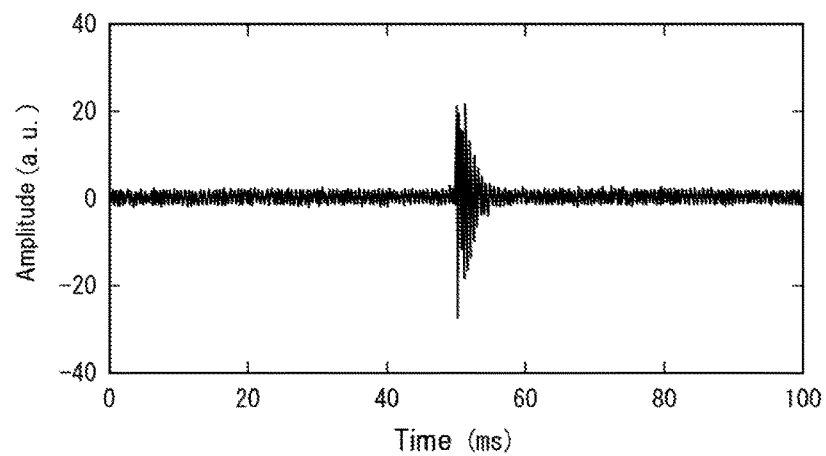

[FIG.3]
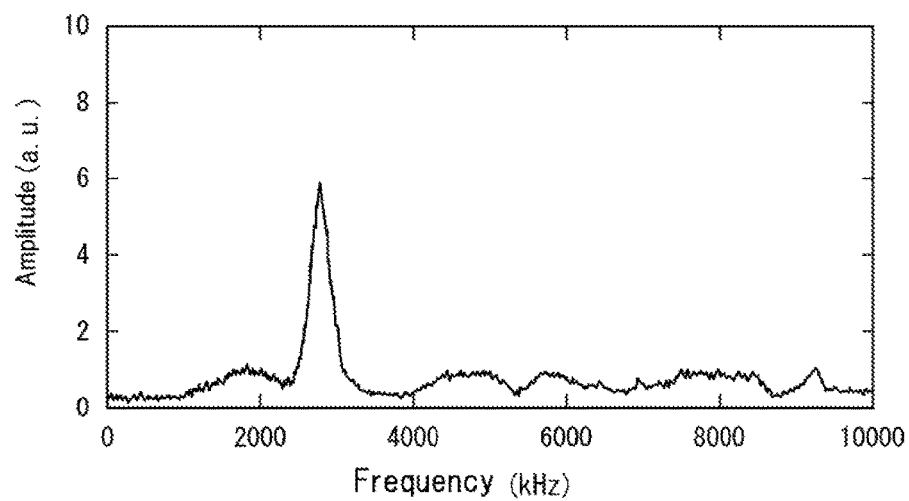
[FIG.4]
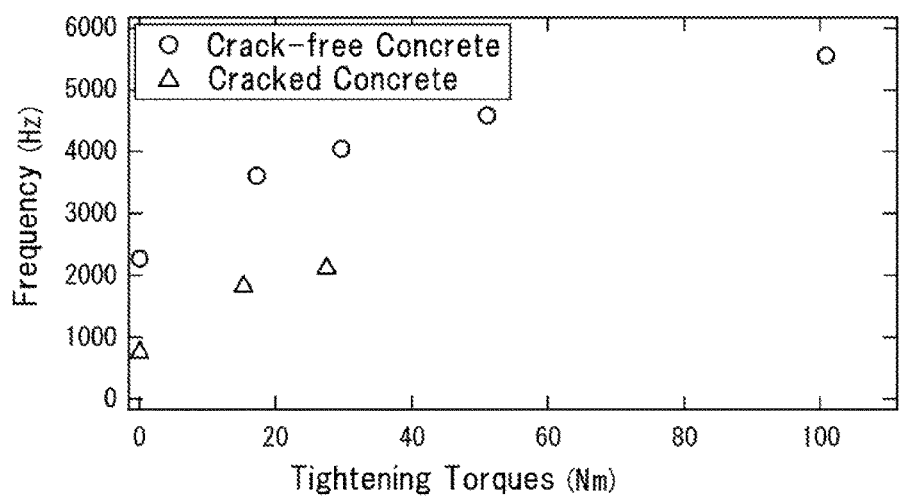

[FIG.5]
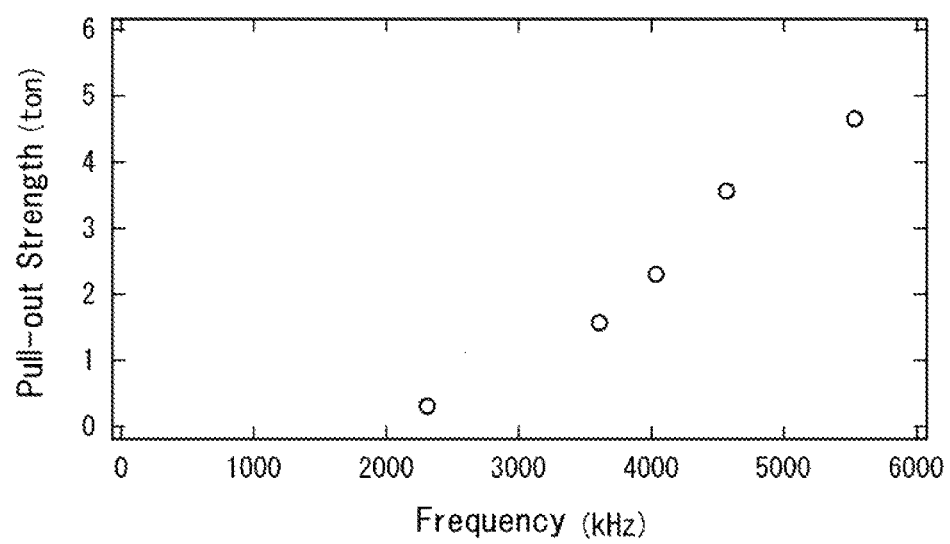

NON-DESTRUCTIVE TESTING METHOD AND A NON-DESTRUCTIVE TESTING DEVICE FOR AN ANCHOR BOLT

FIELD OF THE INVENTION

The present invention relates to a non-destructive testing method and a non-destructive testing device for testing soundness of an anchor bolt fixed to foundation by a metal anchor.

Conventionally, driving type or fastening type metal anchors having an expanding portion have been used for installing and fixing devices or machines on a foundation of, for example, a concrete structure. Specifically, an anchor bolt having an expanding portion is inserted to a hole opened in a foundation, and the expanding portion is expanded, whereby the anchor bolt is mechanically fixed in the foundation.

An anchor bolt fixed by such construction methods may be influenced by inappropriate installation, or could suffer aging degradation, and when left unattended, these may lead to safety problems of the structure.

Here, inappropriate installation may involve looseness of a bolt, a deformed bolt (bent, crooked or the like), insufficient fastening (insufficient driving), insufficient concrete strength and cracks in concrete. Aging degradation may include a deformed bolt (bent, crooked or the like), cracks in the bolt, a bolt breaking, corrosion wastage of the bolt, looseness of a nut, strength deterioration of concrete and cracks of concrete.

From the viewpoint of ensuring safety of the structure, it has been desired to assess soundness of a metal anchor, that is, presence/absence of inappropriate installation or aging degradation, of portions embedded in the concrete structure and not visually observable, in a non-destructive manner. For example, the following methods have been adopted.

Impact noise method is a method, in which the head of an anchor bolt exposed from a concrete surface is hit by a hammer, and based on two factors, that is, the sound generated by the hammer at that time and the feeling of impact through the hammer, an inspector determines presence/absence of any abnormality.

Ultrasonic testing is a method, in which an ultrasonic sensor is mounted on the exposed head of an anchor bolt, and based on a reflection signal from the anchor bolt derived from ultrasonic sound applied to the anchor bolt, defects such as corrosion or flaw of the anchor bolt are determined. This method is widely used in general as a non-destructive testing method (For example, Patent Document 1).

Further, a method has been proposed in which an accelerometer is mounted on the exposed head of an anchor bolt, reflected wave of acoustic wave generated by the impact by the hammer is received by the accelerometer, and based on intensity and time lag of the reflected wave, any damage to the anchor bolt, any rupture in the surrounding concrete or the like is tested (For example, Patent Document 2).

PRIOR ART REFERENCES

Patent Documents

[Patent Document 1] JP2004-77234A
[Patent Document 2] JP2010-203810A

SUMMARY OF THE INVENTION

Problems to be Solved by the Invention

Recently, it is desired to quantitatively assess soundness of an anchor bolt in a non-destructive manner with high accuracy. The methods above, however, cannot be considered sufficient from the point of quantitative assessment.

That is, quantitativeness of the impact noise method largely depends on the skill of the inspector, and, therefore, test results are not very reliable and quantitative testing for soundness of anchor bolts with high accuracy has been difficult. Further, depending on the environment of testing (such as noise environment and the status of anchor bolt installation), there is a possibility that the test itself becomes difficult.

The ultrasonic testing allows inspection of soundness of the anchor bolt itself independent of the inspector's skill. It has been difficult, however, to quantitatively assess inappropriate installation or aging degradation.

In the non-destructive testing method disclosed in Patent document 2, oscillation of elastic wave such as ultrasonic wave is caused from the head of the anchor bolt, and based on the intensity and time lag of reflected wave of the elastic wave, soundness of an anchor bolt or concrete is tested. It has been difficult to measure with high accuracy the intensity and time lag of reflected wave of the elastic wave depending on surface roughness of the anchor bolt or a complicated structure of the anchor bolt such as screw cutting. Thus, this method also has the similar problem.

Therefore, an object of the present invention is to provide a non-destructive testing method and a non-destructive testing device enabling quantitative testing of soundness of an anchor bolt fixed in a foundation by a metal anchor, in a non-destructive manner.

Means for Solving the Problem

The invention according to claim 1 provides
a non-destructive testing method of testing soundness of an anchor bolt fixed in a foundation by a metal anchor, wherein
a portion of said anchor bolt exposed from a surface of said foundation is hit to cause a hitting sound,
a signal waveform of said hitting sound is received and subjected to frequency analysis to obtain frequency information of said signal waveform, and
based on the frequency information of said signal waveform, soundness of said anchor bolt is quantitatively tested in a non-destructive manner.
The invention according to claim 2 provides
the non-destructive testing method according to claim 1, wherein
a portion of said anchor bolt exposed from a surface of said foundation is hit to cause a hitting sound,
the signal waveform of said hitting sound is amplified, before the signal waveform of said hitting sound is subjected to frequency analysis, and
the amplified signal waveform of the hitting sound is subjected to Fast Fourier Transform and thereby frequency-analyzed, to obtain the frequency information of said signal waveform.
The invention according to claim 3 provides
the non-destructive testing method according to claim 1 or 2, wherein
the frequency information of said signal waveform is compared with database including frequency information of signal waveforms of anchor bolts of which soundness has been confirmed beforehand, whereby soundness of said anchor bolt is quantitatively tested.
The invention according to claim 4 provides
the non-destructive testing method according to claim 3, wherein said database is compiled as relations between frequency information of signal waveforms and pull-out strength of anchor bolts.

The invention according to claim 5 provides a non-destructive testing device of an anchor bolt for testing soundness of an anchor bolt fixed in a foundation by a metal anchor, comprising:

a hitting sound generating means for generating a hitting sound by hitting a portion of said anchor bolt exposed from a surface of said foundation;

a sensor receiving the generated hitting sound;

a signal processing device obtaining a signal waveform of the hitting sound received by said sensor and performing frequency analysis of said signal waveform to obtain frequency information of said signal waveform; and a testing device quantitatively testing soundness of said anchor bolt in a non-destructive manner based on the obtained frequency information of said signal waveform.

The invention according to claim 6 provides the non-destructive testing device according to claim 5, wherein said testing device has, as database equipped beforehand, relations between frequency information of signal waveforms and pull-out strength of anchor bolts, and said testing device is configured to evaluate soundness of said anchor bolt by comparing said database with the frequency information of said signal waveform obtained by said signal processing device.

Effect of the Invention

The present invention provides a non-destructive testing method and a non-destructive testing device enabling quantitative testing of soundness of an anchor bolt fixed in a foundation by a metal anchor, in a non-destructive manner.

BRIEF DESCRIPTION OF THE DRAWINGS

FIG. 1 A schematic illustration showing a non-destructive anchor bolt testing device in accordance with an embodiment of the present invention FIG. 2 A graph showing an example of signal waveform of the hitting sound received by the sensor FIG. 3 A graph showing an example of frequency information of the signal waveform obtained from frequency analysis by a signal processing device FIG. 4 A graph showing relations between tightening torques and the frequency information about anchor bolts to be tested FIG. 5 A graph showing relations between frequency information of signal waveforms and pull-out strength about anchor bolts to be tested

EMBODIMENTS OF CARRYING OUT THE INVENTION

Referring to the figures, a non-destructive testing method and a non-destructive anchor bolt testing device regarding an embodiment of the present invention will be described below.

1. Non-Destructive Testing Device

FIG. 1 is a schematic illustration showing a non-destructive anchor bolt testing device in accordance with the embodiment, which includes an impact hammer 2, a sensor 3, and a signal processing device 4. An anchor bolt 5 is inserted to a hole opened in a foundation 10 of a concrete structure and has an expanding portion which is expanded, so that it is fixed in foundation 10.

Specifically, anchor bolt 5 is provided with a stud 51 and a sleeve (expanding portion) 52. Stud 51 has a male screw portion 53 and a wedge 54 for radially expanding sleeve 52. Anchor bolt 5 is inserted to a hole 11 in foundation 10, a nut 55 is screwed onto the male screw portion 53 of stud 51 protruding from foundation 10 and turned, whereby stud 51 and wedge 54 are pulled upward. At this time, sleeve (expanding portion) 52 is radially expanded by wedge 54, so that sleeve 52 bites into a wall surface of hole 11 and fixed in foundation 10. In other words, as wedge 54 moves, sleeve 52 expands and is fixed in foundation 10. Here, reference character "56" represents a washer.

(1) Impact Hammer

Impact hammer 2 is the hitting sound generating means for generating a hitting sound inside anchor bolt 5 by hitting a head portion 5a of anchor bolt 5, such as a nut 55, exposed from the surface of foundation 10. Impact hammer 2 is not specifically limited and a general, commercially available hammer may be used.

(2) Sensor

Sensor 3 is mounted in contact with anchor bolt 5, on an upper surface of head portion 5a of anchor bolt 5, and it receives a signal waveform of the hitting sound generated by the hitting by impact hammer 2. The hitting sound received by sensor 3 is thereafter transmitted to signal processing device 4. As sensor 3, mainly, an AE sensor as a piezoelectric element sensor receiving high frequency component in ultrasonic range (several tens kHz to several MHz) is used. It is not limiting, however, and a general sonic sensor may be used.

(3) Signal Processing Device

Signal processing device 4 is mounted for obtaining the signal waveform of the hitting sound received by sensor 3, performing frequency analysis and thereby obtaining frequency information of the signal waveform. It includes a signal amplifier (amp) for amplifying the signal waveform of the hitting sound transmitted from sensor 3, and a personal computer for analysis, performing frequency analysis of the amplified signal waveform of the hitting sound.

The personal computer for analysis includes signal processing software for analyzing the signal waveform of hitting sound, and by performing frequency analysis such as FFT (Fast Fourier Transform) on the signal waveform of the hitting sound received by sensor 3, frequency information of the signal waveform can be obtained.

Further, in a storage unit of the personal computer for analysis (Not shown in the drawing), frequency information of signal waveforms of anchor bolts, of which soundness has been confirmed beforehand, is obtained in advance through, for example, a mock-up test, and stored as database.

Though a wedge type anchor, which is one of the fastening type metal anchors, has been described as an example, a driving type metal anchor is similar to the fastening type metal anchor in that it is fixed by means of the expanding portion and, therefore, the configuration above can be applied in the similar manner.

2. Non-Destructive Testing Method

Next, the non-destructive testing method of quantitatively testing, in a non-destructive manner, soundness of an anchor bolt fixed in the foundation by a metal anchor, using the non-destructive testing device 1 will be described.

First, head portion 5a of anchor bolt 5 embedded with the head portion 5a exposed from the surface of foundation 10 is hit by impact hammer 2, and whereby a hitting sound is generated in anchor bolt 5.

The generated hitting sound is received by sensor 3 and transmitted to signal processing device 4, by which a signal waveform of the hitting sound is obtained. FIG. 2 shows an example of the obtained signal waveform of the hitting sound. As can be seen from FIG. 2, the signal waveform of the hitting sound generates by the impact of impact hammer 2, and attenuates gradually as time passes.

Then, the signal waveform of said hitting sound is amplified by the signal amplifier of signal processing device 4. Thereafter, the amplified signal waveform of the hitting sound is subjected to FFT using signal processing software installed in the personal computer for analysis of signal processing device 4 and thus frequency-analyzed, whereby frequency information of the signal waveform is obtained. FIG. 3 shows an example of the obtained frequency information of the signal waveform.

As can be seen from FIG. 3, a peak appears at a specific frequency. Therefore, if the frequency at which a peak appears and the peak height are known, it is possible to determine presence/absence of inappropriate installation or aging degradation of the anchor bolt, that is, it is possible to quantitatively assess and test soundness of the anchor bolt.

Here, it is preferred that, as in the present embodiment, the obtained frequency information can be compared with pre-stored database, since it enables quantitative testing of the soundness of an anchor bolt in a shorter time with higher accuracy.

Specifically, if relations between frequency information of the signal waveform and physical properties as an indicator of soundness of anchor bolts are stored in advance as database, the soundness of the anchor bolt can be evaluated by comparing the frequency information of the signal waveform obtained this time by signal processing device 4 with the database. As the physical property used as the indicator, pull-out strength is particularly preferable. If the relations between the frequency information of signal waveforms and the pull-out strength of anchor bolts are compiled as database, soundness of the anchor bolt can easily be evaluated based on the pull-out strength of the anchor bolt.

3. Effects of the Embodiment

According to the present embodiment, based on the frequency information of the signal waveform obtained by frequency analysis of the signal waveform of the hitting sound, soundness of a portion, that cannot directly be observed visually, of the anchor bolt fixed in a foundation by a metal anchor can quantitatively tested in a non-destructive manner.

Specifically, the non-destructive testing device in accordance with the present embodiment aims at quantitative testing soundness of a metal anchor in a non-destructive manner. Considering a metal anchor, the expanding portion of the anchor bolt is in tight contact with the base concrete. Therefore, signal waveform of the hitting sound allowing appropriate frequency analysis can be obtained. Further, since the frequency information obtained from the signal waveform of hitting sound changes reflecting inappropriate installation or aging degradation, it is possible to quantitatively test soundness in a non-destructive manner by using the non-destructive testing device in accordance with the present embodiment.

Further, the frequency information used as the index in the non-destructive testing device of the present embodiment is obtained from the hitting sound derived from eigen frequency of the structure such as concrete or the anchor bolt. Therefore, by the comparison with the database, soundness of even a complicated structure can easily be tested.

Intensity of peak frequency of the frequency information depends, for example, on surface roughness of the anchor bolt. The peak frequency and the intensity ratio of peak frequency, however, do not much depend on the surface roughness. Therefore, different from the reflection wave of an elastic wave, these are independent of the surface roughness of the object to be measured. Thus, highly accurate testing of soundness is possible.

Further, in general, when a device, machine or the like is to be fixed on a foundation such as a concrete structure, it is often the case that the device or machine is connected to an anchor bolt with a nut or a base plate interposed. According to the present embodiment, it is possible to test soundness of the anchor bolt in a non-destructive manner without necessitating removal of such a nut or a base plate.

EXAMPLES

Example 1

1. Preparation of Samples for Example 1

First, normal samples were formed by opening holes of a prescribed size in crack-free concrete and inserting M16 steel anchor bolts, and bad samples were formed by opening holes of a prescribed size in cracked (crack width: about 3 mm) concrete and inserting M16 steel anchor bolts.

1. Evaluation Method

Then, tightening torque of a nut of anchor bolts of both normal samples and bad samples was regulated in five steps from "0" N·m to "100" N·m, and using said non-destructive testing method, frequency information corresponding to the tightening torque was obtained. Results are as shown in FIG. 4.

In FIG. 4, the abscissa represents actually measured tightening torque, and the ordinate represents frequency corresponding to the tightening torque. It is noted, however, that when the tightening torque exceeded 50 N·m in bad samples, concrete was broken. Therefore, results of bad samples with the tightening torque of 50 N·m or higher are not plotted.

TABLE 1

| Tightening torque (N · m) |
|---|
| 0 |
| 15 |
| 30 |
| 50 |
| 100 |

3. Test Results

It can be seen from FIG. 4 that in normal samples with crack-free concrete, the frequency information shifted to the high-frequency side as the tightening torque increased.

On the other hand, in bad samples with cracked concrete, though the frequency information shifted to the high-frequency side as the tightening torque increased, same as in the samples without cracks, the frequency information has lower frequency as compared with the samples without cracks.

Example 2

Next, focusing on the point that inappropriate installation or aging degradation lowers pull-out strength of an anchor bolt, correlation between the frequency information and the pull-out strength was calculated, and experiments were performed to evaluate possibility of testing soundness of an anchor bolt based on the correlation.

1. Preparation of Samples for Example 2

A plurality of samples were prepared by opening holes of a prescribed size in concrete and inserting and fixing M16 steel anchor bolts.

2. Evaluation Method

For each sample, pull-out strength was measured, and the frequency information was obtained using the above-described non-destructive testing method. The results are as shown in FIG. 5.

3. Test Results

It can be seen from FIG. 5 that as the pull-out strength of anchor bolt increased, the frequency information shifted almost linearly to the high-frequency side. Therefore, if this relation is compiled beforehand as database, it is possible to easily know the pull-out strength of an anchor bolt and to evaluate soundness, by comparing the frequency information of the signal waveform obtained this time by the signal processing device with the pre-prepared database.

It can be seen from the results in Example 1 and Example 2 that soundness of an anchor bolt fixed in a foundation by a metal anchor can be tested quantitatively in a non-destructive manner by obtaining the frequency information using said non-destructive testing device and said non-destructive testing method.

The present invention has been described above with reference to the embodiments. However, the present invention is not limited to said embodiments. Various changes may be made on said embodiments within the scope identical or equivalent to that of the present invention.

DESCRIPTION OF THE REFERENCE NUMERALS

1 Non-destructive testing device
2 impact hammer
3 sensor
4 signal processing device
5 anchor bolt
5a head portion
10 foundation
11 hole
51 stud
52 sleeve
53 male screw portion
54 wedge
55 nut
56 washer

What is claimed is:

1. A non-destructive testing method of testing soundness of an anchor bolt fixed in a foundation by a metal anchor, the method comprising:
hitting a portion of said anchor bolt exposed from a surface of said foundation causing a hitting sound,
receiving a signal waveform of said hitting sound and subjecting the signal waveform to frequency analysis to obtain frequency information of said signal waveform, and
quantitatively testing a soundness of said anchor bolt based on the relations between the frequency information of signal waveforms and the pull-out strength of anchor bolts.

2. The non-destructive testing method according to claim 1, the method further comprising:
amplifying the signal waveform of said hitting sound, before the signal waveform of said hitting sound is subjected to frequency analysis, and
subjecting the amplified signal waveform of the hitting sound to Fast Fourier Transform and thereby frequency-analyzing to obtain the frequency information of said signal waveform.

3. The non-destructive testing method according to claim 1, the method further comprising:
comparing the frequency information of said signal waveform with database including frequency information of signal waveforms of anchor bolts of which soundness has been confirmed beforehand, whereby soundness of said anchor bolt is quantitatively tested.

4. The non-destructive testing method according to claim 3, wherein
said database is compiled as relations between frequency information of signal waveforms and pull-out strength of anchor bolts.

5. A non-destructive testing device of an anchor bolt for testing soundness of an anchor bolt fixed in a foundation by a metal anchor, comprising:
a hitting sound generating means configured to generate a hitting sound by hitting a portion of said anchor bolt exposed from a surface of said foundation;
a sensor configured to receive the generated hitting sound;
a signal processing device configured to obtain a signal waveform of the hitting sound received by said sensor and performing frequency analysis of said signal waveform to obtain frequency information of said signal waveform; and
a device configured to quantitatively test soundness of said anchor bolt based on the relations between the frequency information of signal waveforms and the pull-out strength of anchor bolts.

6. The non-destructive testing device according to claim 5, wherein
said testing device includes a database, the database including relations between frequency information of signal waveforms and pull-out strength of anchor bolts, and
said testing device is configured to evaluate soundness of said anchor bolt by comparing said database with the frequency information of said signal waveform obtained by said signal processing device.

* * * * *